United States Patent [19]

Shafer

[11] Patent Number: 4,533,640
[45] Date of Patent: Aug. 6, 1985

[54] ACCUMULATED THERMAL EXPOSURE RESPONDER AND METHOD OF USE

[76] Inventor: Jules A. Shafer, 1038 Baldwin, Ann Arbor, Mich. 48104

[21] Appl. No.: 581,981

[22] Filed: Feb. 21, 1984

[51] Int. Cl.³ .................. G01N 21/78; G01N 21/82
[52] U.S. Cl. ........................ 436/2; 116/207; 206/219; 206/222; 374/102; 422/55; 422/58; 422/61; 426/88; 436/7; 436/147; 436/164
[58] Field of Search ............ 436/1, 2, 7, 147, 164, 436/169, 905; 422/55, 56, 57, 58, 61; 116/206, 207, 216; 374/101, 102, 104, 105, 106, 161, 162; 426/88; 206/219, 222; 215/DIG. 8

[56] References Cited

U.S. PATENT DOCUMENTS

| | | | |
|---|---|---|---|
| 2,787,269 | 4/1957 | Cohen | 206/219 X |
| 2,798,855 | 7/1957 | Hainsworth | 422/57 X |
| 3,344,914 | 10/1967 | Bloom et al. | 215/DIG. 8 |
| 3,576,604 | 4/1971 | Hammond | 436/2 |
| 3,603,469 | 9/1971 | Magni | 215/DIG. 8 |
| 3,968,872 | 7/1976 | Cavazza | 206/222 |
| 3,996,007 | 12/1976 | Fang et al. | 116/206 X |
| 4,066,567 | 1/1978 | Labes | 116/206 X |
| 4,138,357 | 2/1979 | Igarashi | 374/162 X |
| 4,151,748 | 5/1979 | Baum | 116/207 X |
| 4,273,674 | 6/1981 | Ligon, Jr. et al. | 436/7 |

OTHER PUBLICATIONS

Su et al., Journal of Organic Chemistry, vol. 34, pp. 926-929 (1969).
Morawetz et al., J. Am. Chem. Soc., vol. 84, p. 3783 (1962).

*Primary Examiner*—Arnold Turk
*Assistant Examiner*—Robert J. Hill, Jr.
*Attorney, Agent, or Firm*—Krass and Young

[57] ABSTRACT

An adjustable accumulated thermal exposure indicator device, and method of use, for affixing to and indicating deterioration of perishable goods and the like, comprising (1) a reactant yielding material that reacts via one or more steps at a rate depending on time, temperature, and pH to provide an amine and (2) an indicator that reacts at a time, temperature, concentration and pH dependent rate with the amine to produce a visible reaction that is indicative of the expiration of a predetermined time-temperature history related to the useful life of the goods to which the device is affixed. Also provided is a device or article that is responsive to accumulated thermal exposure for the controlled release of immobilized alcohols and amines.

13 Claims, 6 Drawing Figures

ACCUMULATED THERMAL EXPOSURE RESPONDER AND METHOD OF USE

DESCRIPTION

1. Technical Field

The invention relates to a monitor of thermal exposure which visibly signals deterioration or depletion of the useful life of perishable goods and the like. Embodiments of the device are also useful for eliciting controlled release of immobilized amines and alcohols responsive to accumulated thermal exposure.

2. Background of the Invention

The quality or efficacy of perishable packaged foods, photographic film, biologicals, chemicals, pharmaceuticals and other consumable materials is usually dependent on their time and temperature of storage. In an effort to assure the consumer of the freshness of perishable goods, the supplier often stamps expiration dates on these goods to indicate the end of the useful life of the goods. Although the expiration dates usually are conservative estimates of shelf life at recommended storage temperatures, they do not take into account the substantial reductions in shelf life of a product caused by storage at temperatures higher than those recommended that, for example, might be experienced transiently during power outages and breakdowns in refrigeration. High temperatures might also be experienced by individual packages in warm sections of refrigerated showcases or storage compartments or by packages in refrigeration units equipped with inaccurate thermostats. Finally, unaccountable removal and replacement of food, pharmaceuticals and other labile materials from the refrigerator for purposes of transport and use make it difficult to predict the remaining useful lifetime of individual packages of perishables. These uncertainties often lead to premature disposal of perishables or the use of deteriorated perishables. Such practices which can be wasteful of material and labor and in some cases cause a health hazard, could be minimized by devices that would indicate whether perishable goods had accumulated a deleterious amount of thermal exposure.

Many devices have been described for indicating the expiration of shelf-life at a predetermined temperature. Representative devices are those described, for example, U.S. Pat. Nos. 3,966,414, 3,999,946, 4,057,029, 4,212,153, 4,278,561, 4,298,348 and 4,384,980. Generally, these devices rely on chemical reactions or diffusion of indicator dyes through a semipermeable membrane. A serious limitation of most known time-temperature indicators based upon nonenzymatic chemical reactions is their sensitivity to light or impurities such as oxygen, trace metal ions, and other free radical scavengers which contaminate most solvents and chemical reagents. Devices based upon enzymatically catalyzed reactions are likely to be limited by deterioration of the enzymes at rates which are difficult to control. These limitations can affect the reliability of time-temperature indicators based on polymerization of acetylenes, those based on the bleaching of dyes by peroxides and those based on enzymatically catalyzed reactions. The use of diffusion through a permeable plastic membrane also is limited since this process like most diffusion based processes shows little dependence upon temperature. The limitation is partially overcome in devices comprising a diffusion layer capable of transition between an impermeable and permeable liquid crystal state. Above the transition temperature, the devices should indicate the passage of time in a fairly temperature independent fashion characteristic of a diffusion process. Below the transition temperature, little or no diffusion occurs and little or no change in the indicator occurs with passage of time. Although these devices appear to be good indicators for signalling transient exposure to temperatures above the melting point of the membrane, they do not appear to be well suited for reflecting thermal aging of goods which may be exposed to temperatures between 3° and 50° C. during their lifetimes.

It therefore is an object of the present invention to provide improved means for indicating accumulated thermal exposure (ATE) as well as methods of use for indicating the expiration of the useful life of perishable goods and the like.

It also is an object of the invention to provide exposure indicator means yielding a relatively abrupt visible change after a predetermined accumulated thermal exposure has been obtained or yielding a continuously increasing color intensity that is relatable to the accumulated thermal exposure.

Another object of the invention is to provide a time-temperature indicating device that, prior to use, is in a standby mode and, for use as a monitoring device, can be activated to coincide with the onset of aging of the goods to which it is affixed.

Still another object is to provide a device that is responsive to accumulated thermal exposure and affords controlled release of an agent such as a flavor or fragrance.

These and other objects, features, and advantages will be seen from the following description of the invention and by reference to the accompanying drawings and examples.

SUMMARY AND DETAILED DESCRIPTION

The present invention relates to an accumulated thermal exposure (ATE) device, especially a device for affixing to and indicating deterioration of perishable goods and the like.

The device in one preferred embodiment comprises a container in which the contents are viewable, and reagents in the container including a reactant yielding reagent that during the exposure produces an amine reactant and an indicator yielding reagent that during the exposure reacts with the amine to produce after a predetermined accumulated thermal exposure a visible indicator reaction whose onset corresponds to the expiration of the shelf-life of the perishable goods.

The device comprises reagents reacting in a multistep consecutive reaction pathway wherein a reaction which produces a visible change in color or precipitate is the terminal step. This approach allows one to produce a desired lag in the onset of color change or precipitation by appropriate adjustment of rates of reactions in the pathway and initial concentrations of reactants. To ensure that the indicator functions in a reliable fashion, the reaction pathway involves neither free radicals nor catalysis by enzymes for reasons already stated. In the reaction pathway comprising the preferred embodiment of this invention, rates of individual steps in the reaction pathway are dependent not only on temperature, but also on the pH of the reaction medium and the concentration of reagents. Thus by routine trial one, according to the invention, can conveniently preselect the particular combination of pH and reagent concentration in the device to achieve indication of a predetermined time-temperature history, referred to herein as accumulated thermal exposure (ATE), that corresponds closely and reproducibly with expiration of the useful life of a given perishable product. Additionally, by varying the pH and concentrations of reagents one can, according to the invention, vary or preselect the sharpness of the onset of the visible endpoint be it color change or formation of a precipitate. The reaction pathways comprising the preferred embodiments of this invention can be divided into a reactant yielding pathway and an indicator yielding reaction as depicted below.

Example of a reactant yielding pathway:

Examples of indicator yielding reactions:
Formation of a yellow color:

Formation of a precipitate:

Where $Me^{+2}$ is a metal ion such as $Zn^{+2}$ which forms an insoluble complex with anthranilic acid.

The reactant yielding material for purposes of this invention is any suitable material that decomposes via one or more steps at a pH, time, and temperature dependent rate to produce an amine which in turn reacts with an indicator reagent and thereby produces a change in color or a precipitate. For this purpose, a preferred reactant yielding material is a substituted or unsubstituted cyclic imide such as N-2'-carboxyphenylphthalimide, phthalimide, or maleimide. Also preferred is a phthalamic acid such as N-2'-carboxyphenylphthalamic acid. Another preferred reactant yielding material is an amide of a dicarboxylic acid such as phthalic acid or maleic acid where the second carboxylic acid group is free or is derivatized as an ester or an amide. The indicator reagent material in one preferred embodiment is one which reacts with the amine produced in situ to provide a visible reaction which appears as a color. A preferred indicator for the purpose is 2-chloro-3,5-dinitrobenzoic acid. The indicator reagent in another preferred embodiment is one that reacts with the amine produced in situ to provide a visible reaction which appears as the formation of a precipitate. A preferred indicator for the purpose is a suitable metal ion such as zinc contained in aqueous buffered solution. The usefulness of the pathway comprising reactions A, B and $C_1$ or A, B and $C_2$ in the ATE indicator of the invention depends upon several unexpected and unique features of the reagents and intermediates that need to be appreciated to formulate the ATE indicator properly. These features are described as follows:

Reaction A: In the pH range 4–7, the rate constant for reaction A is about 2 days$^{-1}$ at 25° C. This rate constant which has not been reported previously, is unexpectedly large for hydrolysis of a substituted phthalimide in this pH range. For example, the rate constant for the hydrolysis of N-methylphthalimide is about 0.1 days$^{-1}$ at pH 6.5, as reported by S.C.K. Su and J. Shafer, J.Org.Chem. 34, 926–929 (1969). This rate constant decreases with decreasing pH. The reason for the facile hydrolysis of N-2'-carboxyphenylphthalimide remains to be established. Above pH 7–8, the rate constant for hydrolysis of N-2'carboxyphenylphthalimide increases with increasing pH.

Reaction B: In the pH range 3–10, amide II undergoes hydrolysis at rates which are several orders of magnitude higher than those of simple amides. The facile hydrolysis of amide II has been attributed to anchimeric assistance from the two carboxyl groups, as reported by H. Morawetz and J. Shafer, J. Am. Chem. Soc. 84, 3783 (1962). The primary rate enhancement is from a protonated phthalic acid carboxyl group and the secondary enhancement from an unprotonated carboxylate group on the anthranilic acid residue. The rate constant for reaction B at 25° C. is about 0.8 days$^{-1}$ at pH 5.4. This rate constant is markedly dependent on pH. Increases in pH above pH 5.4 result in a decrease in the rate constant by about 10-fold per unit increase in pH. Rate constants that are about an order of magnitude higher than that observed at pH 5.4 can be obtained at pH values near 4.

Reaction $C_1$: Unlike reactions A and B which follow first order rate laws in buffered solutions, reaction $C_1$ follows a second order rate law. In other words, it is first order with respect to the concentration of amine and first order with respect to the concentration of the indicator reagent. Thus, the half life for reaction $C_1$ is dependent on the concentration of these reagents. When one reagent is present in large excess, the half life of reaction $C_1$ is inversely proportional to the concentration of the reagent in excess. Under these conditions, pseudo first order kinetics are observed where the pseudo first order rate constant is equivalent to the product of the second order rate constant and the concentration of amine or indicator reagent, whichever is present in large excess. The second order rate constant for the reaction between IV and V is dependent on pH in a manner which suggests that the monoanion of anthranilic acid (IV) is about 20 times more reactive than the neutral form of IV and that the cationic form of anthranilic acid (IV) is unreactive toward the indicator reagent (V). Second order rate constants of about 6 and 11 $M^{-1}$ days$^{-1}$ at pH 5.4 and 6.6 respectively have been observed for the reaction between IV and V. An important and unexpected property of the indicator 2-chloro 3,5-dinitrobenzoic acid (V) is that it reacts with anthranilic acid and other amines at rates useful for ATE indicators at ambient temperatures and below, while the indicator reagent by itself is stable in the aqueous reaction buffers. Several other activated aromatic halides such as 2,4-dinitrochlorobenzene were tried and found to be unsuitable. They hydrolyzed with elimination of halide ion to the corresponding yellow phenolate at substantial rates and thereby short circuited the pathway for production of yellow color.

Reaction $C_2$. This reaction is used when it is desired to signal ATE by formation of a precipitate. The onset of precipitation does not occur until sufficient anthranilic acid has been liberated so as to exceed the solubility product of the 1:2 metal ion anthranilate salt. Thus, increasing the concentration of I and metal ion will decrease the ATE which results in the onset of precipitation. When this reaction is employed, care must be taken in the choice of pH and buffer to avoid precipitation of metal hydroxides and metal salts of buffer ions. Addition of chelating agents such as dicarboxylic acids can also be used to prevent precipitation of metal ion hydroxides.

General considerations: The color intensity exhibited by an ATE indicator after a given accumulated thermal exposure can be increased by increasing the concentrations of either reagent I or V or by decreasing the sum of the half times for reactions A, B, and $C_1$. This sum can be conveniently varied over a wide range by varying the pH of the reaction medium and the concentration of reagents I or V, whichever is in excess. The choice of the pH of the reaction medium usually has the greatest effect on the half time for reaction B and the initial concentration of excess reagent determines the half time of reaction $C_1$. By systematically changing the sum of the half times of reactions A, B and $C_1$ while keeping the value of the half time of reaction $C_1$ close to that of reaction B, one can usually maximize the abruptness of the color change exhibited by the indicator when a desired accumulated thermal exposure is reached. At temperatures of 25° C. and below and at most pH values, the rate constant for reactions A and C decrease by a factor of about 2 per 10° C. decrease in temperature whereas the rate constants observed for reaction B decrease by a factor of about 3 to 4 per 10° C. decrease in temperature. When desirable, kinetic reaction thereby that is art-recognized can be employed to calculate the time dependence of color intensity at 410 nm of an ATE indicator at a given temperature from the rate constants for the individual steps of the pathway, and the molar absorptivity of VI (about $1.7 \times 10^4$ $M^{-1}$cm$^{-1}$ at 410 nm).

As already indicated, the time and sharpness of the onset of appearance of yellow color or precipitate can be adjusted by varying the pH of the reaction medium and the concentration of reagents. These parameters are adjusted further, according to a preferred embodiment of the invention, by starting with an ester VIII instead of I in reaction $A_1$, as follows:

VIII where R is, but is not restricted to, an alkyl group such as methyl, ethyl, benzyl or menthyl group. This reaction, which is pH dependent, extends the reactant yielding pathway since VIII is converted to I in aqueous buffers. The pathway can be shortened by starting with II instead of I, so as to decrease further the time and sharpness of the appearance of the visible indicator. Alternatively, if it is desired to continuously build up visible color intensity linearly with product age, one starts with V and an amine such as IV at the appropriate concentration and pH value to yield the desired rate of build up of color intensity.

Additionally, the rates of steps in the pathway can be modulated further using substituents on the phthalic acid nucleus and/or anthranilic acid nucleus in the compounds described in this invention. For certain uses, such as those where it is desired to obtain a visible color change only after very large accumulated thermal exposures, N-alkylphthalimides such as N-methylphthalimide can be used in place of N-2'-carboxyphenylphthalimide. Maleic acid and substituted maleic acids can also be used instead of the phthalic acid grouping. Finally, the facile elimination of alcohol in reaction $A_1$ and the carboxyl and carboxamide-facilitated elimination of amines from mono or diamides of dicarboxylic acids can be used for controlled release of flavors, insecticides, animal attractants or repellants, fragrances, pharmaceuticals, analytical reagents, and other materials. For example, reaction of the ester VIII where R represents menthyl can be used to release a peppermint-like flavor or fragrance at a rate which is controlled by the pH of the reaction medium.

As the ATE indicator is activated and thereafter exposed to ambient storage and use temperatures, it accumulates an integrated exposure history of its own, corresponding to the aging or depletion of the useful life of perishables which it is monitoring or to which it is affixed. In this regard, a significant feature of the device is the provision of means for the user, whether a supplier of the goods or a consumer or other user, to activate the ATE indicator. The ability of the supplier of goods to activate the indicator is important when the indicator is to be used to signal improper handling of perishable goods during transport to the customer. For the consumer, the ability to activate the indicator is important where the onset of aging occurs when the package seal is broken. Additionally, the ability to activate the indicator after it is manufactured facilitates stockpiling of indicator devices for activation and use at a later date.

A preferred embodiment comprises a nonfrangible, in other words non-breakable, common container or envelope containing a separate frangible container. As shown in the accompanying drawings and described in greater detail hereinafter, the common container is flexible and its contents are visible to the user so that, to activate the device, the common container is flexed or stressed sufficiently to bend and break the frangible container contained within thereby allowing for the mixing of the previously separate content of these containers so that the device from that point in time is thereby activated for subsequent accumulated thermal exposure measurement. The common container can be in any suitable form and made of any suitable material such as a plastic packaging material. In one preferred embodiment, the container is a commercially available polyethylene plastic sample tube (rated capacity 0.4 ml., 4 mm inside diameter) equipped with a polyethylene cap, the capped tube being heat sealed to make it tamper proof. The frangible container can be in any suitable form and made of any suitable material such as a glass or plastic packaging material. In one preferred embodiment, the frangible container is a commercially available sealed glass capillary tube of suitable dimension (for example, 25 mm in length by 1.3 mm ID × 1.7 mm. OD).

Another preferred embodiment of the ATE indicator device, as shown in the drawings, comprises a container; a first closure for sealing the container defining a membrane having opposed faces with one face open to the container, the other closure face having a recess; and a second closure insertable in one position in the recess for telescopically matching and sealing engagement with the recess, and further having puncture means and movable to a second position in the recess with the puncture means advanced telescopically in piercing relation through the membrane so that liquid contents in the container can be mixed with liquid contents in the recess of the first closure. A preferred embodiment is one in which the reactant yielding reagent and the reaction buffer together with the indicator yielding reagent, one preferably contained in the container and the other in the recess of the second closure, are kept separate prior to activation.

The purpose of the two compartments is to keep the reactant yielding reagent in an inert medium prior to activation of the ATE indicator. For this purpose, the reactant yielding reagent can be kept in a suitably inert medium. N-2'-carboxyphenylphthalimide (I), for example, can be kept in ethanol which as an inert medium is adequate for most purposes. The reactant yielding material can also be in one compartment in the solid state. For most applications the indicator reagent can be in either container.

The invention in another preferred aspect relates to a device or article that is responsive to accumulated thermal exposure, for the controlled release of an immobilized alcohol, or an amine, comprising a polymeric derivative of formula IX, X, XI XII or XIII:

derivable from an alcohol ROH or an amine RNH$_2$ where ROH and RNH$_2$ may be a pharmaceutical, analytic reagent, flavor, fragrance, insectide, animal attractant or repellent, and where R' in IX is, but is not restricted to, an alkyl group such as methyl, ethyl or benzyl; and an aqueous buffer having a predetermined pH; the polymeric derivative being hydrolyzable to provide the alcohol or amine at a rate that is dependent on pH, time and temperature. The invention also contemplates a device or article in which the phthalic acid residue of the polymeric derivative is nuclearly substituted or is replaced by another dicarboxylic acid residue such as maleic acid, capable of forming a cyclic imide. A preferred device or article is one in which ROH is menthol and the polymeric material is aminoethyl cellulose.

The invention is another preferred aspect relates to a process employing an indicator device as described above, comprising the steps of selecting the device for its indicator reaction corresponding to the given shelf-life and activating the device contemporaneously with the step of affixing the device to said perishable goods. By these means, the useful life of the device advantageously can be timed to start at the beginning of the useful life of the fresh goods. In other words, the lives of the device and the goods are in phase.

The invention in another preferred embodiment relates to a non-visably perishable product (that is, a product that by outward signs alone cannot be evaluated, such as a packaged dairy product) having affixed thereto an indicator device, as described, activated in phase with the expected useful life of the product. In one preferred embodiment, the indicating device is activated to produce a visible yellow color reaction upon expiration of a predetermined time-temperature history corresponding to the expected useful life of the product.

DESCRIPTION OF THE DRAWINGS

Referring to the drawings.

Figure 1:
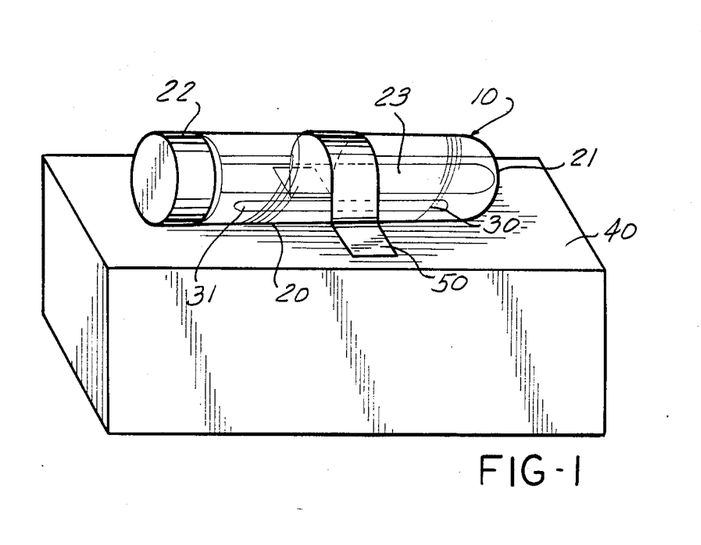
FIG. 1 is a view of a preferred embodiment of an indicator device according to the invention, affixed to a package containing a perishable product.
Figure 2:
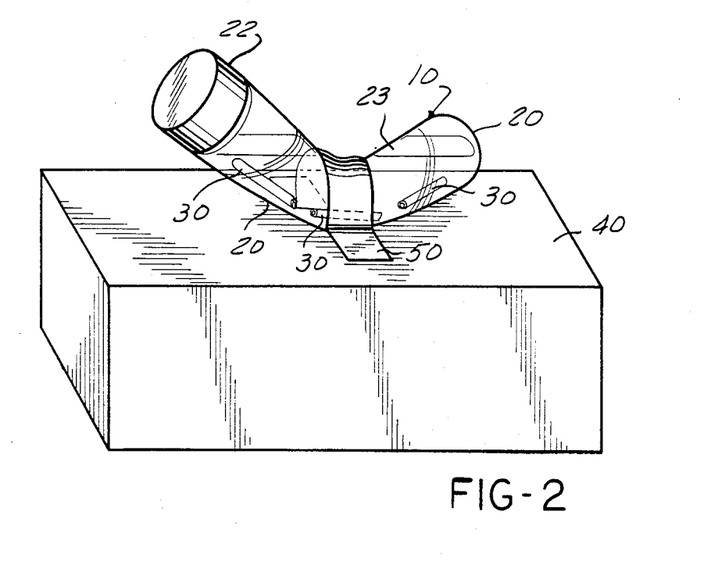
FIG. 2 is a similar view illustrating how the device is activated by flexing the outer container of the device of FIG. 1 and thereby selectively breaking the inner container of the device for mixing the contents of the inner and outer containers.

As shown in FIG. 1, the indicator device 10 has an outer or common container 20 tubular or cylindrical in shape with a closed end 21 and an opposite open end sealed by a telescopically fitted cap 22. The container 20 is structurally semi-rigid but flexible with regain so that the container flexes when bent as shown in FIG. 2. The container 20 is partly filled with a liquid 23 and contains an inner container 30 which is also tubular or cylindrical in shape and sealed at both ends. As shown, the inner container is visible from the outside of the device 10. The inner container 30 in turn contains a liquid 31 and is in contact with the liquid 23 of container 30 but the liquids 23 and 31 are kept separate until the device is activated. The inner container is rigid and breakable under stress. The device 10 as shown is affixed to a package 40 by an adhesive tape 50 so that it is kept with the package during the useful life of its contents, the purpose being to expose the device 10 and the packaged contents to the same conditions of time and temperature during the useful life of the packaged contents. To activate the device 10, as shown in FIG. 2, the outer container 20 is bent or flexed until the inner container 30 is fractured thereby releasing its contained liquid 31 with the result that the liquids 23 and 31 are in contact and can be mixed. At this point, the device begins to monitor the time-temperature history of the packaged contents, and in due course the device signals by a visible color reaction, as described above, the expiration of the useful life of the packaged contents.

Figure 3:
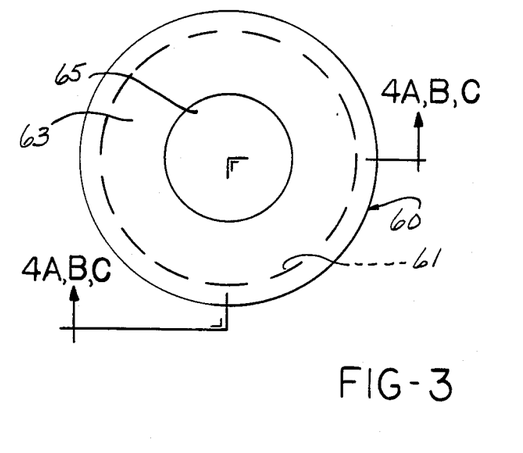
FIG. 3 is a top view of another preferred embodiment of an indicator device according to the invention.
Figure 4A:
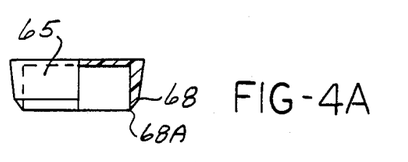
FIGS. 4a, 4b, and 4c are side views of the latter device, partly in section, taken on line 4—4 of FIG. 3.
Figure 4B:
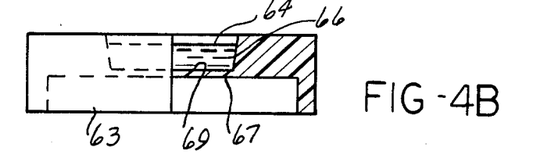
Figure 4C:
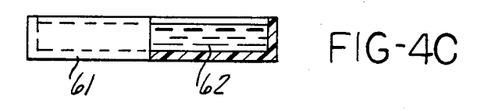

Another preferred embodiment of the indicator device, which allows for activation of the indicator at time selected by the user, is shown in FIG. 3. The device 60 comprises a container dish 61 that serves to contain a liquid 62, a cap 63 for the dish having, on what may be regarded as its top side, a recess 64 that serves as a second container, and a hollow plug 65 that fits telescopically into, and thereby seals, the recess 64. Recess 64 contains a liquid or solid 66. The central portion of the underside of the cap 63 constitutes an impermeable membrane 67 that is pierceable. In this regard, the plug 65 has a shoulder 68 that is tapered inwardly and serves as a cutting edge 68a at what may be regarded as its lower surface. The plug 65 functions, when telescoped into the recess 64, in two positions (not shown): one in which the plug is partly telescoped into the recess so that the cutting edge 68a is resting at or just above the top surface 69 of the membrane 67 and the other in which the plug is telescoped farther into the recess so that the cutting edge is pushed through (made to pierce) the membrane 67 thereby dislodging the membrane from the center of the cap. In using the device, the dish 61 is filled with a selected quantity of liquid 62 containing one reagent. The dish is then sealed with the cap 63.

A second liquid or solid 66 containing another reagent is filled into the recess 64 of the cap and the recess is sealed with the plug 65 in a first or standby position where the shoulder edge 68a is resting at or just above the top surface 69 of the membrane 67. To activate the device, for purposes of monitoring the shelf-life of perishable goods according to the invention, one simply affixes the devices to the goods and pushes the plug 65 farther into the recess so that, while maintaining a leak proof seal, the cutting edge 68a pushes through the membrane 67 and thereby causes the liquids 62 and 66 to be contacted together and mixed. In due course, with the expiration of the predetermined shelf-like, the exposed mixture responds to produce a visible reaction that is an indicator of the mentioned expiration. The device can be made of any suitable materials such as acrylic plastic (e.g., Plexiglas). In general, the dimensions are not critical. Conveniently, the membrane is about 0.6 inches in diameter and about 6 mils thick. The seals between the component parts of the device can be press fit seals so that the assembled device is leakproof without more. If desired, an adhesive or solvent can be used to make the cap/dish seal tamper-proof.

The invention in preferred embodiments is described, and the best mode of practicing the same is set forth, in the following examples.

EXAMPLE 1

Activated ATE Indicator Packaged with Perishables Having Useful Shelf-Lives of 25 to 100 Days at 3° C. and 2 to 8 Days at 25° C.

A batch of 4 mm. ID polyethylene tubes are filled to contain individually 250 microliters (ul) of pH 5.4 0.4M sodium acetate buffer mixed with 20 ul of a solution containing 20 mM N-2'-carboxyphenylphthalimide and 100 mM 2-chloro-3,5-dinitrobenzoic acid in 95% ethanol, and the liquid is sealed in the tubes with a heat seal. The activated ATE indicator tubes are each immediately affixed by taping or other means to individual batched packages of 25- to 100-day refrigerator perishable goods. For these indicator tubes, a faint yellow color typically is visible after 2 days at room temperature (25° C.) or 25 days at refrigerator temperature (3° C.). To facilitate interpretation of the indicator color with respect to the quality of a particular product, a colored band is printed on the package to indicate the color intensity at which the product is no longer useful. For dated goods, the appearance of early expiration of the indicator serves as a warning that the item has been handled improperly. When desirable, as for monitoring goods with longer shelf-lives, the rate of appearance of yellow color can be delayed by increasing the pH of the reaction buffer.

EXAMPLE 2

An Activatable Accumulated Thermal Exposure Indicator for Signalling the Deterioration of Perishables with Shelf-Lives of 25 to 100 days at 3° C. and 2 to 8 days at 25° C.

A sealed glass capillary tubing (25 mm long by 1.3 mm ID) containing 20 ul of a solution composed of 20 mM N-2'-carboxyphenylphthalamide and 100 mM 2-chloro-3,5-dinitrobenzoic acid in 95% ethanol is placed together with 250 ul of pH 5.4, 0.4M sodium acetate buffer in a 0.4 ml polyethylene sample tube (4 mm ID) which is then fitted with a polyethylene cap. The capped tube is heat sealed to make it tamper proof. The indicator is activated at the desired time by bending the polyethylene tube so as to shatter the internal glass capillary tubing and mix the contents. The activated device is affixed to the goods to be monitored either prior to activation or contemporaneously. After activation, this indicator exhibits a time dependent buildup of yellow color which matches that of the freshly prepared indicator of Example 1. After activation, the use of this activatable indicator is the same as that of the indicator described in Example 1.

EXAMPLE 3

Determination of the Extent of Thermal Exposure of Goods to Temperatures above 3° C.

A color chart (of the type, for example, shown below) supplied with the indicator enables the user to determine the deviant thermal exposure of the indicator to temperatures above 3° C. The user matches the color of the indicator to a color on the chart. A row of numbers alongside the color gives the deviant accumulated thermal exposure (DATE) for indicators of various ages, where the age of the indicator is the time in days since its activation. The deviant accmulated thermal exposure (DATE) is defined as the time in days at 25° C. necessary to elicit the deviant (above 3° C.) accumulated thermal exposure exhibited by the indicator. An indicator kept at 3° C. typically shows a DATE of zero when its color and age is matched to the chart. The ability to estimate DATE thereby facilitates location of the point at which perishable goods have been mishandled with respect to refrigeration as well as estimation of their remaining useful life.

| CHART FOR ESTIMATING DEVIANT ACCUMULATED THERMAL EXPOSURE (DATE) FROM INDICATOR COLOR AND AGE | | | | | |
|---|---|---|---|---|---|
| Yellow Color | Age (Days) | | | | |
| Intensity | 10 | 20 | 30 | 40 | 50 |
| Faint | 0.8 | 0 | — | — | — |
| Light | 1.7 | 0.8 | 0 | — | — |
| Medium | 2.7 | 1.7 | 0.8 | 0 | — |
| High | 4.0 | 2.7 | 1.7 | 0.8 | 0 |

EXAMPLE 4

An Activatable ATE Indicator for Signalling Deterioration of Perishables with Shelf-Lives of 1 to 4 months at 25° C. and 0.5 to 2 months at 37° C.

A sealed glass capillary tubing (25 mm long by 1.3 mm ID) containing 20 ul of a solution composed of 26 mM N-2'-carboxyphenylphthalimide and 15 mM 2-chloro- 3,5-dinitrobenzoic acid in 95% ethanol is placed together with 250 ul of pH 7.30, 0.1M sodium phosphate buffer in a 0.4 ml polyethylene sample tube (4 mm ID) to which a polyethylene cap is then heat sealed. The device is activated in a manner similar to that described for the device of Example 2. A typical viewer definitely detects a faint yellow color at 37° C. at two weeks after activation. At 25° C., a faint yellow color is definitely detected at about one month after activation. To facilitate interpretation of the indicator color with respect to the quality of the particular product, a colored band is printed on the package to indicate the color intensity at which the product is no longer useful. When desired, considerable increases in the time for the onset of visible color and rate of build-up of color can be achieved by using buffered soloutions (e.g. borate buffer) at pH values above 8.5 as the reaction medium.

EXAMPLE 5

An Indicator for Signalling Thermal Exposure of Goods during Short Term Storage and Shipping.

A sealed glass capillary tubing (25 mm long by 1.3 mm ID) containing 20 ul of 20 mM N-2'-carboxyphenylphthalamic acid dissolved in 40 mM NaOH (to convert it to the disodium salt), is placed together with 250 ul of 32 mM 2-chloro-3,5-dinitrobenzoic acid in pH 5.57, 0.4M sodium acetate buffer in a 0.4 ml polyethylene sample tube (4 mm ID). The filled tube is capped with a polyethylene cap and heat sealed. The device is activated at the desired time by bending the polyethylene tube so as to shatter the internal glass capillary tubing and mix the contents. The activated device is affixed to the goods to be monitored either prior to activation or contemporaneously. Within 6 to 8 hours of exposure to a temperature of 25° C., a faint yellow color becomes visible to the average viewer. The color increases in intensity continuously and reaches half full intensity in about 3 days. At refrigerator temperature (3° C.) a faint yellow color becomes visible in 3 days which increases to about half full intensity in about 30 days. The half full intensity color is an unmistakenly bright yellow and corresponds to an absorbance at 410 nm of 5 in the 4 mm pathlength tube.

For perishable goods undergoing refrigerated transport for less than 3 days duration, the absence of more than a faint yellow color can be interpreted to indicate that no deleterious mishandling with respect to refrigeration has occurred during transport. When desirable, the time necessary for producing the onset of the appearance of detectable yellow color can be reduced by an order of magnitude by increasing the final concentration of N-2'-carboxyphenylphthalamic acid and/or 2-chloro-3,5-dinitrobenzoic acid in the activated device. Thus, exposure of perishable goods to room temperature for periods of less than one hour can be detected.

EXAMPLE 6

Activated ATE Indicator Paper

A batch of filter paper squares 1×1 cm are soaked with a cold freshly prepared solution of pH 5.4 0.4M acetate buffer containing 2 mM N-2'-carboxyphenylphthalimide and 20 mM 2-chloro-3,5-dinitrobenzoic acid and 9% ethanol. The wet filter paper squares are placed in small plastic bags fabricated from transparent polyethylene film or other suitable material. Without heating the paper, the bags are heat sealed to provide a vapor proof chamber for the wet paper. Immediately thereafter, the bags are affixed to the individual batched goods; this is done with a heat seal at an area not occupied by the wet paper. The paper turns light yellow after about two days at 25° C. and becomes more intensely yellow over the next week. At a refrigeration temperature of 3° C., the paper begins to develop a yellow color in about 25 days. The time for yellow color to develop can be increased by decreasing the concentration of 2-chloro-3,5-dinitrobenzoic acid or by increasing the pH of the buffer. To facilitate interpretation of the indicator color with respect to the quality of a particular product, a colored band is printed on the package to indicate the color intensity at which the product is no longer useful as described in Example 1.

EXAMPLE 7

Activatable ATE Indicator Paper

In a batchwise procedure, a 1×1 cm square of filter paper such as S & S #589 filter paper is soaked with 80 ul of pH 5.4, 0.4M acetate buffer containing 22 mM 2-chloro-3,5-dinitrobenzoic acid. The wet filter paper is placed in a small plastic bag as described in Example 6. A piece of commercially available plastic polyethylene tubing, for example 1.14 mm ID and 1.57 mm OD sealed at one end with paraffin (3–5 ul) and containing 8 ul of 22 mM N-2'-carboxyphenylphthalimide in 95% ethanol, is sealed on the other end by application of heat. The resulting sealed tube is placed in the plastic bag together with the filter paper square and the bag is heat sealed. The sealed bag is suitable for attaching to perishable goods for purposes of monitoring. At the desired time, either before or after the bag is affixed to the goods, the paper is activated by applying finger pressure to the polyethylene tubing, so as to break the paraffin seal and push the solution out of the tube and onto the wet paper without breaking the plastic bag. After activation, the characteristics and use of this indicator are the same as that described for the indicator in Example 6.

EXAMPLE 8

An Indicator for Estimating the Accumulated Thermal Exposure and the Remaining Useful Life of Solutions of Laboratory Reagents.

This example illustrates the preparation and use of an indicator device for use with reagents that are prepared in analytical and research laboratories and that have limited lifetimes. Such reagents are usually stored in the refrigerator and are periodically removed to be dispensed. The reagents usually deteriorate more rapidly at the elevated temperatures at which they are dispensed. Since it is inconvenient to log accurately the time at which the reagent is kept at laboratory temperature, most reagents are discarded well before their useful life has expired, or they are periodically prepared in small amounts that are used up long before they begin to deteriorate. The indicator device is prepared by mixing 300 ul of 5.88 mM anthranilic acid in pH 4.2, 0.4M acetate buffer with 2.7 ml of 5.8 mM 2-chloro-3,5-dinitrobenzoic acid in a 1×1 cm commercially available polystyrene disposable cuvet equipped with a screw cap. The cuvet is capped and affixed to the reagent bottle via string from the cap of the cuvet to the neck of the reagent bottle so that when desired the cuvet can be easily detached from the reagent bottle by unscrewing the cap. The indicator solution in the cuvet continuously yellows with age. The absorbance at 410 nm of the indicator solution reaches a value of 2 after 42 days of exposure at 25° C. or at about 6 months of exposure at a refrigerator temperature of 3° C. For the first 20 days of exposure at 25° C. the absorbance at 410 nm increases 0.05 per day to allow easy estimation of the accumulated thermal exposure of the reagent from the absorbance of the indicator solution. The accumulated thermal exposure (ATE) is defined as the number of days at 25° C. which would be required to elicit the same thermal exposure as that accumulated by the reagent. A reagent which has been kept continuously at 3° C. for 6 months typically exhibits an ATE of 42. For most reagents the maximal permissible thermal exposure at 25° C. can be estimated or determined empirically. Thus, the remaining useful lifetime of a reagent can be estimated at any time from the difference between its maximal permissible thermal exposure (in days) and its ATE as determined from the absorbance of the indicator solution. In cases where the absorbance reading is greater than one (ATE greater than 20 days), accumulated thermal exposure (ATE) is calculated from the relationship.

$$ATE = 199\ln[10/(10 - Abs_{410})]$$

where 10 is the value of $Abs_{410}$ when all the anthranilic acid has reacted.

For reagents which have low maximal permissible thermal exposures at 25° C., one uses an indicator solution which shows a relatively greater increase in absorbance with increasing exposure at 25° C. An indicator solution which increases 0.24 absorbance units per day (0.01 absorbance units per hour) at 25° C. for the first 4 days is prepared in the same manner as the first solution except that the concentration of 2-chloro-3,5-dinitrobenzoic acid is increased by 0.24/0.05, or 4.8 fold. With this indicator, the ATE is obtained using the equation $$ATE = 41.5\ln[10/(10 - Abs_{410})]$$

It is important to note that both indicators yield the same ATE value when exposed to the same conditions, and that indicators can be prepared which become yellow at rates intermediate, or faster than, the rates of these two indicators by adjustment of the final concentration of anthranilic acid.

EXAMPLE 9

An Activatable ATE Indicator for Signalling Deterioration of Perishables with Shelf Life of 25 Days at 3° C. or One Week at 25° C.

A 0.45 ml portion of a solution consisting of 30 mM zinc acetate dissolved in pH 5.4, 0.4M acetate buffer is added to the dish component of the previously described 3-piece container. The dish is sealed to its cover, and 0.05 ml of a solution containing 500 mM N-2'-carboxyphenylphthalamic acid dissolved in 0.1M sodium hydroxide is placed in the cavity of the cap. The third piece, the plug, is fitted into the cavity so as to provide a leak proof seal. Whn it is desired to activate the indicator, a few pounds of pressure are applied to the plug so as to break the frangible membrane separating the contents of the cavity and dish. After about 25 days at 3° C., a precipitate becomes visible. The onset of visible precipitation occurs within one week at 25° C. The onset of precipitation can be altered by varying the pH of the reaction medium or the concentration of reactants.

EXAMPLE 10

Immobilization and Controlled Release of Alcohols of Commercial Value such as Pharmaceuticals, Analytical Reagents, Flavors, Fragrances, Insecticides, Animal Attractants and Repellents and the like: Immobilization and Controlled Release of Methol.

Menthyl hydrogen phthalate, formed by reaction of phthalic anhydride with menthol, is covalently linked to aminoethylcellulose by reaction with ethyldimethylaminopropyl carbodiimide at pH 4.8 in the cold to yield the menthylated cellulose derivative Xa:

where R is menthyl. The menthylated cellulose is washed and dried by lyophilization. When the menthylated cellulose is wetted with aqueous buffer, menthol is released at a rate which is controlled by the pH of the buffer. The rate of release of menthol is increased by an order of magnitude per pH unit increase above pH 6. The wet menthylated cellulose can be used as a long lasting air freshener or when made up in pharmaceutical dosage form, for application to the skin, it can be used to obtain sustained antipruritic activity or mild local anesthetic activity for relief of painful sprains and the like. A convenient dosage form for topical use is a waterproof adhesive strip bandage having a dressing pad or facing containing the menthylated cellulose in an amount that, when wet with buffered solution is hydrolyzed in sustained fashion to release a pain-relieving quantity of methanol. In this case, to prevent evaporation to the air, the dressing pad incorporates a vapor-impermeable plastic film. By the same procedure, other alcohols can be substituted for menthol for the immobilization and controlled release of the selected alcohol. Also, other amine containing polymers can be substituted for aminoethylcellulose. In a related application, menthol and other alcohol flavors can be linked via an analogous reaction to the amino groups in the polymeric materials used for formulating chewing gum to obtain in an otherwise conventional gum formulation a chewing gum product having a long lasting flavor or sustained release flavor.

EXAMPLE 11

Immobilization and Controlled Release of Amines of Commercial Value such as Pharmaceuticals, Analytical Reagents, Flavors, Fragrances, Insecticides, Animal Attractants and Repellents, and the Like: Immobilization and Controlled Release of Propyl p-aminobenzoate.

1,2,4-Benzenetricarboxylic anhydride is heated with the amine, propyl p-aminobenzoate, to yield XIV.

This compound is covalently linked to aminoethylcellulose at pH 4.8 using ethyldimethylaminopropyl carbodiimide so as to form the cellulose derivative XIIa:

The cellulose derivative is washed with water and the water removed by lyophilization. When the cellulose derivative is wetted with buffered solution, the amine propyl p-aminobenzoate is released at a rate which is controlled by the pH of the buffer. The release of the amine involves two pH dependent reactions, namely hydrolysis of the imide XIIa to a mixture of phthalamic acid derivatives, which mixture in turn hydrolyzes to release the amine. These two reactions are analogous to the above described reaction A and B. The wet cellulose derivative can be applied topically to the skin as described for the menthylated cellulose in Example 10 so as to obtain a sustained anesthetic and antipruritic effect of the amine. Similar reactions are used to obtain immobilization and controlled release of any of a variety of other amines. Also, amine containing polymers other than that in compound XIIa can be substituted for aminoethylcellulose. The amine aspartame, a synthetic sweetener, is linked in this way to the amino groups of polymeric materials used for formulating chewing gum to provide a chewing gum formulation affording sustained release of sweetness.

What is desired to claim as my exclusive property and privilege in the invention, as described, is the following.

I claim:

1. A device for monitoring accumulated thermal exposure and for affixing to perishable goods having a given shelf-life and for signaling the expiration of the given self-life by producing a visible indicator reaction after a predetermined accumulated thermal exposure corresponding to the given shelf-life comprising a sealed container and reagents in said container, wherein the reagents in said container are viewable and include (1) a reactant yielding reagent that is capable of producing an amine reactant during thermal exposure and (2) an indicator yielding reagent that, during thermal exposure, is capable of reacting with the amine to produce a visible indicator reaction after a predetermined accumulated thermal exposure.

2. A device according to claim 1 where the reactant yielding reagent comprises N-2′-carboxyphenylphthalimide.

3. A device according to claim 1 where the reactant yielding reagent comprises N-2′-carboxyphenylphthalamic acid.

4. A device according to claim 1 where the reactant yielding reagent comprises a substituted or unsubstituted cyclic imide.

5. A device according to claim 1 where the indicator yielding reagent comprises 2-chloro-3,5-dinitrobenzoic acid and is capable of reacting with the amine to produce a yellow color.

6. A device according to claim 1 where the indicator yielding reagent comprises an ionic metal or a metal containing compound that is capable of forming an insoluble visible precipitate complex with the amine.

7. A device according to claim 1 where the reactant yielding reagent comprises an N-2′-carboxyphenylphthalamic acid ester of formula where R is a benzyl, menthyl or alkyl group and wherein the reactant yielding reagent also controllably releases an alcohol having a formula ROH.

8. A device according to claim 1 where the reagents are included in an aqueous reaction medium at controlled pH and reagent concentration.

9. A device according to claim 1 wherein the container comprises a non-frangible common container and a separate frangible container located and visible within the common container, wherein the reagents are kept separate within respective containers prior to activating the device by mixing the reagents and wherein the device can be activated by breaking the frangible container.

10. A device according to claim 1 wherein the container includes; a first closure for sealing the container and having opposed faces with one face open to the container and the other closure face having a recess with a bottom, and wherein the bottom of said recess defines a membrane, and a second closure having puncture means and insertable in the recess in two positions, one position for telescopically matching and sealing engagement with the recess, and the second position wherein the puncture means is advanced telescopically in the recess and in piercing relation through the membrane so that liquid contents in the container can be mixed with liquid contents in the recess of the first closure.

11. A method of indicating an accumulated thermal exposure of a device according to claim 1 comprising the steps of subjecting the reactant yielding reagent to said exposure to produce the amine reactant and further reacting the amine reactant thus produced with the indicator yielding reagent to produce a visible reaction.

12. A process of monitoring accumulated thermal exposure of perishable goods having a given shelf-life, employing a device according to claim 1, comprising the steps of selecting the device for its indicator reaction corresponding to the given shelf-life, affixing the selected device to said perishable goods, activating the device by mixing the reagents in the container contemporaneously with the step of affixing the device to said perishable goods and monitoring the device for its indicator reaction.

13. A process according to claim 12 where the device produces a visible yellow color reaction after a predetermined accumulated thermal exposure corresponding to the shelf-life of the perishable goods.

* * * * *

UNITED STATES PATENT AND TRADEMARK OFFICE
CERTIFICATE OF CORRECTION

PATENT NO. : 4,533,640

DATED : August 6, 1985

INVENTOR(S) : Jules A. Shafer

It is certified that error appears in the above–identified patent and that said Letters Patent are hereby corrected as shown below:

Column 1, line 46, insert --in-- between "example," and "U.S.";

Column 14, line 48, delete "whn" and insert --when--;

Column 14, line 63, delete "methol" and insert --menthol--;

Column 15, line 26, delete "methanol" and insert --menthol--; and

Column 16, line 30, delete "self-life" and insert --shelf-life--.

Signed and Sealed this

Nineteenth Day of November 1985

[SEAL]

Attest:

Attesting Officer

DONALD J. QUIGG

Commissioner of Patents and Trademarks